(12) United States Patent
Locke

(10) Patent No.: US 12,728,042 B2
(45) Date of Patent: Sep. 8, 2026

(54) SUPER-ABSORBENT ADVANCED WOUND DRESSING WITH DRESSING FULL INDICATION

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 248 days.

(21) Appl. No.: 18/739,687

(22) Filed: Jun. 11, 2024

(65) Prior Publication Data

US 2024/0325204 A1 Oct. 3, 2024

Related U.S. Application Data

(62) Division of application No. 17/294,667, filed as application No. PCT/US2019/061992 on Nov. 18, 2019, now Pat. No. 12,036,096.

(Continued)

(51) Int. Cl.

| | |
|---|---|
| ***A61F 13/00*** | (2024.01) |
| ***A61F 13/02*** | (2024.01) |
| ***A61F 13/0206*** | (2024.01) |

(52) U.S. Cl.

CPC .... *A61F 13/00055* (2013.01); *A61F 13/0209* (2013.01); *A61F 13/0263* (2013.01); *A61F 13/0289* (2013.01)

(58) Field of Classification Search

CPC ............ A61F 13/01021; A61F 13/0226; A61F 13/00059; A61F 13/00055;

(Continued)

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

European Examination Report for Corresponding Application No. 19827872, mailed Jan. 27, 2022.

(Continued)

*Primary Examiner* — Catharine L Anderson
*Assistant Examiner* — Nhu Q. Tran

(57) ABSTRACT

A wound dressing includes a hydrophilic foam layer, a drape layer, superabsorbent projections, and printed indicators. The hydrophilic foam layer is configured to engage a wound bed and has a first side and a second side, the second side configured to face the wound bed. The drape layer has a first side and a second side, the second side configured to face the first side of the hydrophilic foam layer. The plurality of non-contiguous superabsorbent projections are fixed to and extend from the first side of the hydrophilic foam layer towards the second side of the drape layer. The one or more non-contiguous printed indicators surround one or more of the plurality of superabsorbent projections.

18 Claims, 5 Drawing Sheets

Related U.S. Application Data

(60) Provisional application No. 62/770,128, filed on Nov. 20, 2018.

(58) Field of Classification Search
CPC .. A61F 2013/00153; A61F 2013/00731; A61F 2013/0074; A61F 2013/530802; A61F 2013/00851; A61F 2013/00604; A61F 2013/00634; A61F 2013/00744; A61F 2013/00778; A61F 13/0263; A61F 13/0289; A61F 13/00991; A61F 13/05; A61F 13/00063; A61F 13/0206; A61F 13/022; A61F 13/0223; A61F 2013/00748; A61F 13/0213; A61M 27/00; A61M 1/916; A61M 2025/0266; A61M 1/74; A61M 1/85; A61M 1/77; A61M 1/96; A61M 1/732; A61M 1/71; A61M 1/90; A61M 1/982; A61M 1/73; A61M 2205/583; A61M 2205/584; A61B 90/39
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2005/0256479 A1* 11/2005 Carlucci ................. A61F 13/42 604/362
2006/0149198 A1* 7/2006 Liu ......................... A61F 13/42 604/361
2011/0054429 A1* 3/2011 Lademann .......... A61F 13/0203 604/372
2011/0270206 A1* 11/2011 Jensen .................. A61L 15/425 604/369

(56) References Cited

U.S. PATENT DOCUMENTS

| | | | |
|---|---|---|---|
| 2014/0163491 | A1 | 6/2014 | Schuessler et al. |
| 2015/0080788 | A1 | 3/2015 | Blott et al. |

FOREIGN PATENT DOCUMENTS

| | | | |
|---|---|---|---|
| AU | 755496 | B2 | 12/2002 |
| CA | 2005436 | A1 | 6/1990 |
| DE | 2640413 | A1 | 3/1978 |
| DE | 4306478 | A1 | 9/1994 |
| DE | 29504378 | U1 | 9/1995 |
| EP | 0100148 | A1 | 2/1984 |
| EP | 117632 | A2 | 9/1984 |
| EP | 161865 | A2 | 11/1985 |
| EP | 358302 | A2 | 3/1990 |
| EP | 1018967 | A1 | 7/2000 |
| EP | 2872086 | A1 | 5/2015 |
| FR | 2985569 | A1 | 7/2013 |
| GB | 692578 | A | 6/1953 |
| GB | 2195255 | A | 4/1988 |
| GB | 2197789 | A | 6/1988 |
| GB | 2220357 | A | 1/1990 |
| GB | 2235877 | A | 3/1991 |
| GB | 2329127 | A | 3/1999 |
| GB | 2333965 | A | 8/1999 |
| JP | 4129536 | B2 | 8/2008 |
| SG | 71559 | | 4/2002 |
| WO | 80/02182 | A1 | 10/1980 |
| WO | 8704626 | A1 | 8/1987 |
| WO | 90010424 | A1 | 9/1990 |
| WO | 93009727 | A1 | 5/1993 |
| WO | 94020041 | A1 | 9/1994 |
| WO | 9605873 | A1 | 2/1996 |
| WO | 9718007 | A1 | 5/1997 |
| WO | 9812996 | A1 | 4/1998 |
| WO | 9913793 | A1 | 3/1999 |

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

SUPER-ABSORBENT ADVANCED WOUND DRESSING WITH DRESSING FULL INDICATION

CROSS-REFERENCE TO RELATED APPLICATIONS

This application is a Divisional of U.S. application Ser. No. 17/294,667, filed May 17, 2021, which is a U.S. National Stage Entry of PCT/US2019/061992, filed Nov. 18, 2019, which claims the benefit of priority to U.S. Provisional Application No. 62/770,128, filed Nov. 20, 2018, each of which are incorporated herein by reference in their entirety.

BACKGROUND

The present disclosure relates generally to a wound dressing. The present disclosure relates more particularly to a wound dressing having a hydrophilic foam layer and a drape layer, wherein the hydrophilic foam layer is placed on the wound bed and includes a plurality of non-contiguous superabsorbent projections extending towards the drape layer and one or more non-contiguous printed indicators surrounding one or more of the superabsorbent projections and configured to provide an indication as to when the wound dressing has reached a maximum absorption capacity.

It is often desirable to remove fluid from a wound bed to promote the healing of the wound. In some cases, wound dressings include a layer of foam configured to absorb the fluid from the wound bed. However, the absorption capacity of the wound dressing is often times quite low, such that not all of the wound fluid is absorbed into the wound dressing.

There is often no consistent way to indicate when the wound dressing has reached its fluid absorption capacity. Sometimes a caregiver may not replace the wound dressing as often as desired, or the caregiver may replace the wound dressing too frequently which may retard the healing process, cause additional damage to the wound bed, or cause pain to the patient. Additionally, the dressings often release the absorbed fluid upon removal of the dressing back into the wound bed. The foam layer of the wound dressing may be inadequate in retaining the absorbed wound fluid. It would be beneficial to provide a Super Absorbent Wound Dressing with an indicator that shows when the dressing is full.

SUMMARY

One implementation of the present disclosure is a wound dressing including a hydrophilic foam layer, a drape layer, a plurality of non-contiguous superabsorbent projections, and one or more non-contiguous, printed indicators surrounding one or more of the plurality of superabsorbent projections. The hydrophilic foam layer is configured to engage a wound bed, and has a first side and a second side, the second side configured to face the wound bed. The plurality of non-contiguous superabsorbent projections are fixed to and extend from the first side of the hydrophilic foam layer towards the second side of the drape layer. The one or more non-contiguous, printed indicators surround one or more of the plurality of superabsorbent projections.

Another implementation of the present disclosure is a method of making a wound dressing. The method includes providing a hydrophilic foam layer configured to engage a wound bed and having a first side and a second side, wherein the second side is configured to face the wound bed. The method further includes preparing and applying a slurry including a superabsorbent material on the first side of the hydrophilic foam layer in a plurality of non-contiguous deposits. The method further includes printing one or more non-contiguous indicators onto the first side of the hydrophilic foam layer, such that the indicators surround one or more of the plurality of deposits. The method further includes placing a drape layer, having a first side and a second side, atop the hydrophilic foam layer.

Another implementation of the present disclosure is a method of treating a wound. The method includes providing a dressing configured to cover the wound, the dressing including a hydrophilic foam layer having a plurality of non-contiguous superabsorbent deposits and one or more non-contiguous printed indicators surrounding a corresponding one or more of the superabsorbent deposits. The method further includes observing, on the dressing, an amount of swelling of the superabsorbent deposits in response to the absorption of exudate from the wound. The method further includes replacing the dressing when edges of the swollen superabsorbent deposits approach the printed indicators within a predetermined range.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to FIGS. 1-8, a wound dressing is shown, according to exemplary embodiments. The wound dressing of the exemplary embodiments has multiple layers including a hydrophilic foam layer and a drape layer. The hydrophilic foam layer includes a plurality of non-contiguous superabsorbent projections (e.g., segments, patches, islands, etc.) configured to draw a wound exudate fluid through the hydrophilic foam layer. The hydrophilic foam layer further includes one or more non-contiguous printed indicators surrounding at least one of the superabsorbent projections configured to provide an indication as to when the wound dressing has reached its maximum absorption capacity.

Advantageously, the superabsorbent projections of the hydrophilic foam layer increase the absorptivity of the wound dressing while retaining flexibility. In some embodiments, the superabsorbent projections comprise a plurality of nodules, dots, bumps, lumps, islands, and protuberances extending from the hydrophilic foam layer towards the drape layer. The superabsorbent projections increase the absorption of the wound dressing to wick wound fluid exudate from the wound bed, through the hydrophilic foam layer, and towards the drape layer. Additionally, the drape layer may further act to increase the evaporation rate of wound fluid exudate from the wound dressing. In some embodiments, the drape layer may be free of adhesives, allowing for greater evaporation of wound fluid exudate from the hydrophilic foam layer through to the atmosphere surrounding the drape layer.

Another advantage provided by the wound dressing of the present disclosure is an indication of when the wound dressing has reached its absorption capacity of wound fluid exudate. In some embodiments, the superabsorbent projections are configured to swell upon absorbing the wound exudate fluid, which provides a visual indication of which portion of the wound dressing has absorbed wound exudate and/or when the wound dressing has absorbed a maximum capacity of wound exudate. As the superabsorbent projections swell upon absorption of wound exudate fluid, they expand outwards towards the printed indicators which surround at least one of the superabsorbent projections. The printed indicators provide a visual indication of when the wound dressing has reached maximum fluid capacity once the superabsorbent projections have expanded to the printed indicators. This is intended to provide an indication to a caregiver as to when a wound dressing should be replaced and to further prevent unnecessary changing of the wound dressing. In addition, the superabsorbent projections may shrink away from the printed indicators as the wound exudate beings to evaporate from the wound dressing. Additional features and advantages of the wound dressing are described in detail below.

Wound Dressing

Figure 1:
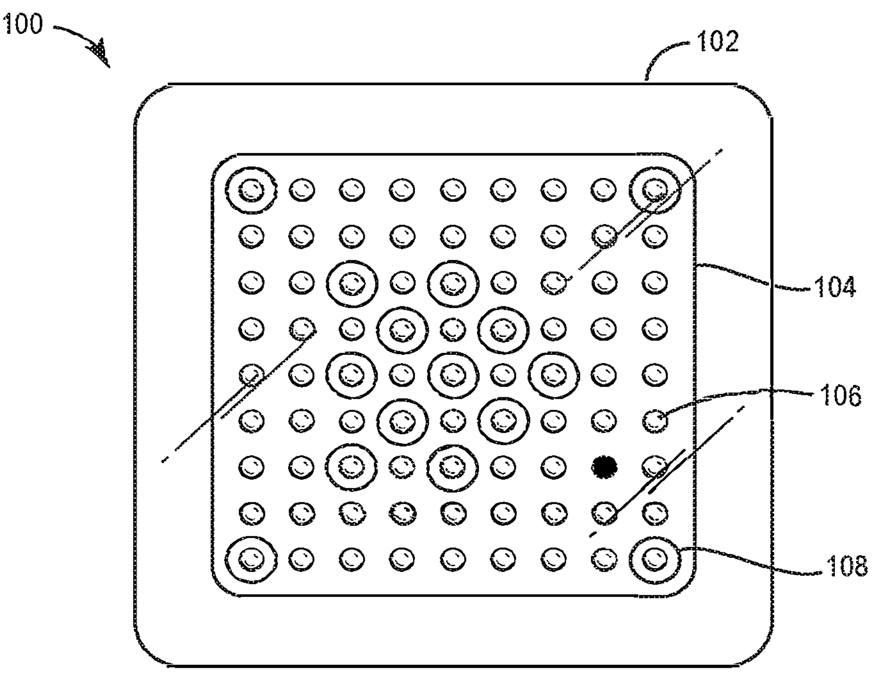
FIG. 1 is a top view of a wound dressing, according to an exemplary embodiment.
Figure 2:
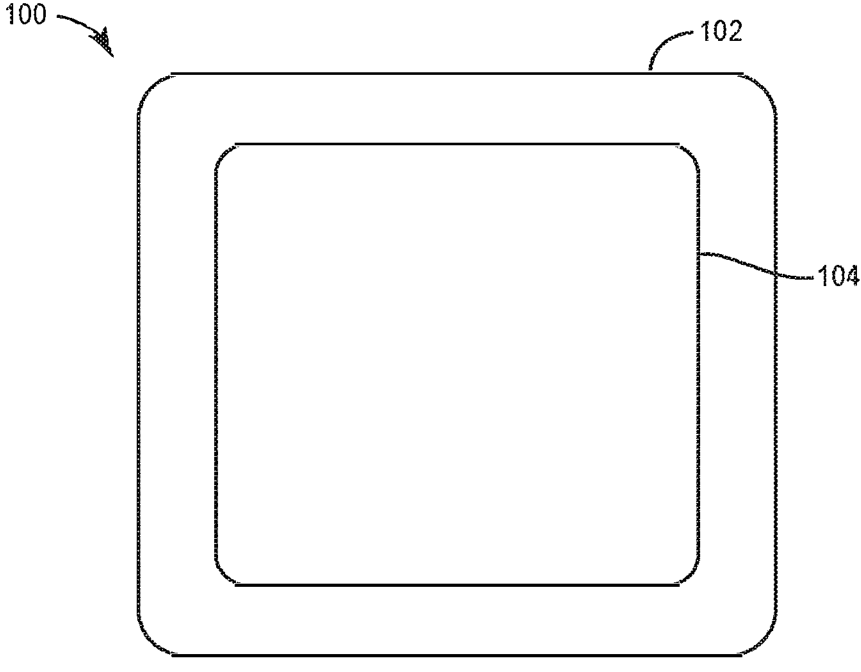
FIG. 2 is a bottom view of the wound dressing of FIG. 1, according to an exemplary embodiment.
Figure 3:
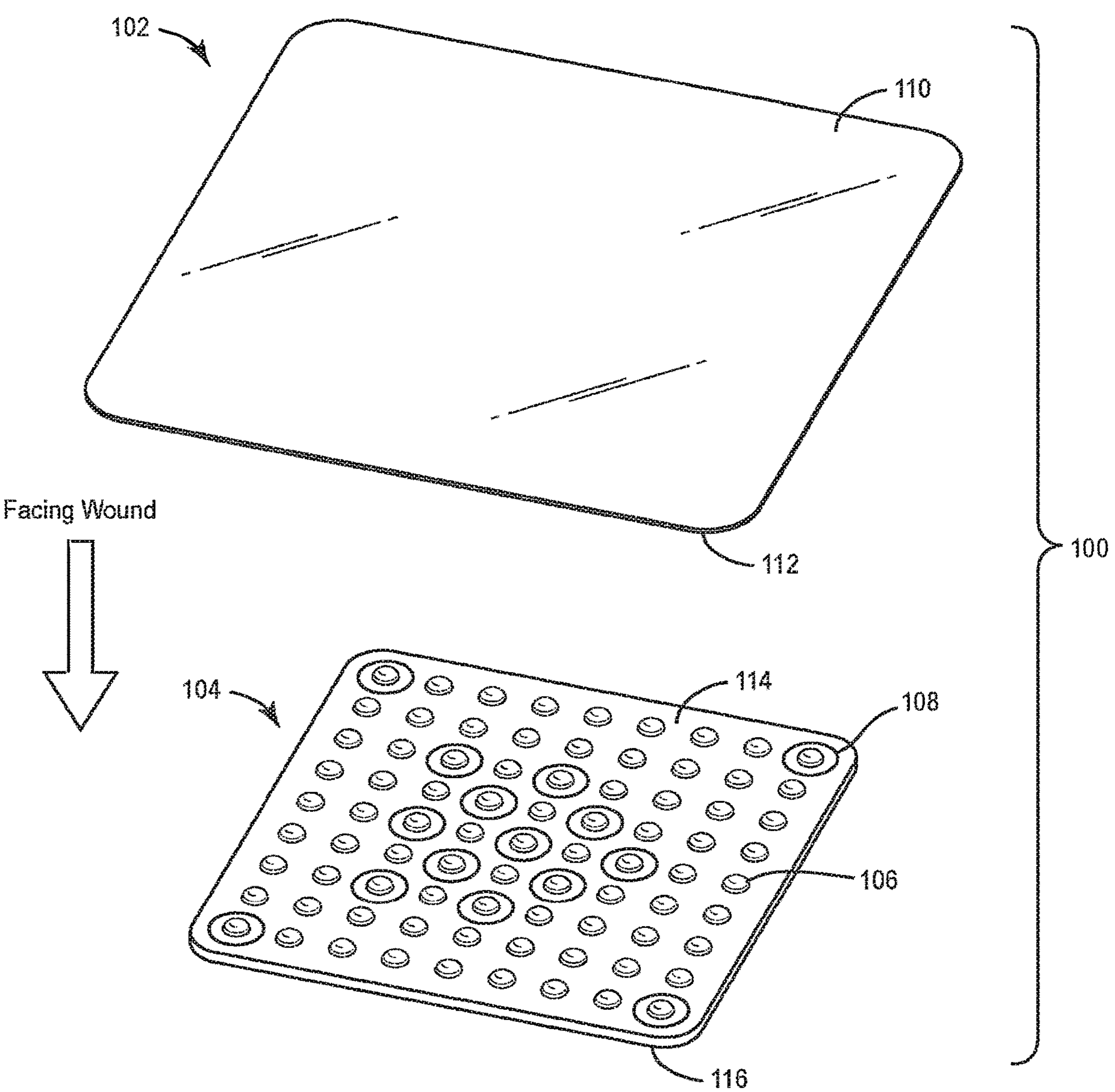
FIG. 3 is an exploded view illustrating several layers of the wound dressing of FIGS. 1-2, according to an exemplary embodiment.
Figure 4:
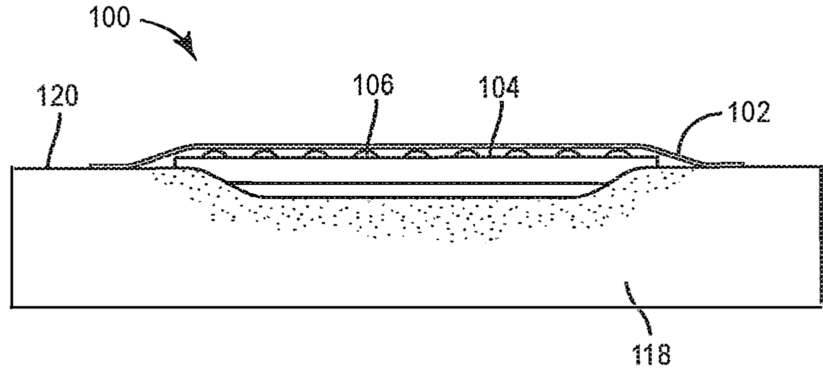
FIG. 4 is a cross-sectional view illustrating several layers of the wound dressing of FIGS. 1-2, according to an exemplary embodiment.

Referring now to FIGS. 1-4, a wound dressing 100 is shown according to an exemplary embodiment. In a brief overview, FIG. 1 is a top view of the wound dressing 100 as would be visible when wound dressing 100 is adhered to a surface (e.g., a patient's skin). FIG. 2 is a bottom view of wound dressing 100 showing the surface of wound dressing 100 configured to contact a wound. FIG. 3 is an exploded view illustrating several components and layers 102-108 of wound dressing 100. FIG. 4 illustrates one embodiment of a cross-sectional view of wound dressing 100 adhered to a patient at a wound bed.

In various embodiments, wound dressing 100 can be formed as a substantially flat sheet for topical applications to wounds, or formed as a contoured dressing for application to body surfaces having high curvature. The size and shape of wound dressing 100 can vary depending on the size of the wound to be dressed and its location. For example, it is contemplated that the size of wound dressing 100 can range from approximately 1 $cm^2$ to 100 $cm^2$, and more preferably from approximately 4 $cm^2$ to 100 $cm^2$. However, other shapes and sizes of wound dressing 100 are also possible depending on the intended use. In other embodiments, wound dressing 100 may have a substantially convex or concave shape, or other customizable topography to adhere to wounds located on areas such as the knee or elbow.

Wound dressing 100 is shown to include (among other possible layers) a drape layer 102, a hydrophilic foam layer 104, a plurality of non-contiguous superabsorbent projections 106, and one or more printed indicators 108 (which may also be non-contiguous) surrounding the superabsorbent projections 106. In other embodiments, wound dressing 100 may include any number of additional layers, such as a perforated film layer or an elastic foam layer. In the embodiment shown, the printed indicators 108 surround only a portion of the superabsorbent projections 106, particularly the superabsorbent projections 106 located in a central portion and the corner portions of wound dressing 100. In other embodiments, the printed indicators 108 may surround each of the superabsorbent projections 106. In the embodiment shown, the printed indicators 108 are printed onto the hydrophilic foam layer 104. In other embodiments, the printed indicators 108 are printed onto the drape layer 102. In some embodiments, the drape layer 102 and the hydrophilic foam layer 104 are bonded to each other (e.g., laminated together using a fusible fiber). In the embodiment shown in FIG. 4, wound dressing 100 is applied for use at the wound bed 118, with the layers 102-104 extending beyond the perimeters of the wound bed 118 and adhering to a top of the periwound 120. In other embodiments, one or both of the layers 102-104 may lie entirely within the confines of the periwound 120. However, other configurations of the locations and layers are also possible depending on the intended use.

Drape Layer

In some embodiments, wound dressing 100 includes a drape layer 102. Drape layer 102 is shown to include a first side 110 and a second side 112 opposite first side 100. Second side 112 is configured to face a wound. When wound dressing 100 is applied to a wound, first side 110 faces away from the wound whereas second side 112 faces towards the wound. Drape layer 102 attaches over hydrophilic foam layer 104, such that second side 112 of drape layer 102 contacts a first side 114 of hydrophilic foam layer 104. Second side 112 of drape layer 102 may also contact, in various locations, superabsorbent projections 106. In some embodiments, the imprints made by superabsorbent projections 106 may be seen on first side 110 of drape layer 102, such that the first side 110 of drape layer 102 has a plurality of bumps. In some embodiments, drape layer 102 is substantially free of adhesives.

In some embodiments, drape layer 102 is laminated to hydrophilic foam layer 104 using a fusible fiber positioned between drape layer 102 and hydrophilic foam layer 104. The fusible fiber may act to isolate and maintain the position of the superabsorbent projections 106 between the drape layer 102 and hydrophilic foam layer 104. Drape layer 102 can be bonded to hydrophilic foam layer 104, for example, by an adhesive or by radiation cross-linking. In some embodiments, drape layer 102 is bonded to the hydrophilic foam layer 104 by urethane or urea linkages. This can be achieved by applying drape layer 102 to hydrophilic foam layer 104 (substantially without mixing) before polyurethane curing is complete. In other embodiments, drape layer 102 may be laminated with a fusible fiber to hydrophilic foam layer 104. In some embodiments, drape layer 102 may be laminated with a fusible fiber to both hydrophilic foam layer 104 and superabsorbent projections 106. In the embodiment shown in FIGS. 1-2, the perimeter of drape layer 102 extends beyond (e.g., circumscribes) the perimeter of hydrophilic foam layer 104 to provide a margin for wound dressing 100 (e.g., as an "island" dressing) to the skin of a patient adjacent to the wound being treated, and may further comprise an adhesive on the second side 112 configured to attach to the wound. In other embodiments, such as is shown in FIGS. 5-8, the perimeter of drape layer 102 is even with the perimeter of hydrophilic foam layer 104.

In some embodiments, drape layer 102 is a thin layer(s) of polyurethane film. One example of a suitable material for drape layer 102 is the polyurethane film known as ESTANE 5714F. Other suitable polymers for forming drape layer 102 include poly alkoxylalkyl acrylates and methacrylates, such as those described in Great Britain Patent Application No. 1280631A filed Nov. 22, 1002, the entire disclosure of which is incorporated by reference herein. In some embodiments, drape layer 102 includes a continuous layer of a high-density blocked polyurethane foam that is predominantly closed-cell. In some embodiments, drape layer 102 may have a thickness in the range of 10 μm to 100 μm.

Drape layer 102 may be substantially permeable to liquid and moisture vapor. In other words, drape layer 102 may be permeable to both water vapor and liquid water such as wound exudate. Such permeability is intended to facilitate or enhance a hydrophilic gradient from the wound bed 136, through the wound dressing 100, and to the surrounding atmosphere. In some embodiments, drape layer 102 is impermeable to bacteria and other microorganisms. In other embodiments, drape layer 102 is configured to wick moisture from hydrophilic foam layer 104 and superabsorbent projections 104 to first side 110 of drape layer 102, such that it may evaporate into the atmosphere. In some embodiments, drape layer 102 may be substantially hydrophilic and have a high moisture vapor transmission rate, such as to permit evaporation of would exudate/fluid from first side 110 of drape layer 102.

Hydrophilic Foam Layer

In some embodiments, wound dressing 100 includes hydrophilic foam layer 104. Hydrophilic foam layer 104 is shown to include a first side 114 and a second side 116 opposite the first side 114. First side 114 of the hydrophilic foam layer 104 is configured to face and, in some embodiments, attach to second side 112 of drape layer 102 wile second side 116 is configured to face a wound bed 118. In some embodiments, first side 114 of hydrophilic foam layer 104 is laminated via fusible fiber to second side 112 of drape layer 102.

Hydrophilic foam layer 104 may comprise a polyurethane foam or a polyethylene foam. In some embodiments, hydrophilic foam layer 104 includes a flexible plasticized hydrophilic polymer matrix having an internal cellular structure. Several examples of hydrophilic foams which can be used to make hydrophilic foam layer 104 are described in detail in U.S. Pat. No. 8,097,272 issued Jan. 17, 2012, U.S. Pat. No. 8,664,464 issued Mar. 4, 2014, and U.S. Pat. No. 8,058,499 issued Nov. 15, 2011. The entire disclosure of each of these patents is incorporated by reference herein. In other embodiments, hydrophilic foam layer 104 may be formed from aromatic or aliphatic precursors. Advantageously, hydrophilic foam layer 104 may provide enhanced absorbency for liquid exudate. This is because the porous structure of the foam provides for rapid uptake of liquid exudate. In some embodiments, hydrophilic foam layer 104 may comprise a fluid reactive dye configured to provide a visual indication of the fluid absorption within wound dressing 100. Several examples of fluid reactive dyes which may be used within hydrophilic foam layer 104 include antherquinone, cothenile, and tartrazine. In some embodiments, hydrophilic foam layer 104 may comprise a fluid-triggered wax in the form of additional printed indicators 108. The fluid-triggered wax may only trigger when hydrophilic foam layer 104 has reached a level of hydration at which skin damage may occur, providing a further warning to a user that both the superabsorbent projections 106 and the hydrophilic foam layer 104 have reached maximum absorption capacity.

Hydrophilic foam layer 104 is shown to include a plurality of non-contiguous superabsorbent projections 106 distributed on the first side 114. In the embodiments shown, superabsorbent projections 106 are substantially evenly distributed along first side 114 of hydrophilic foam layer 106. In other embodiments, superabsorbent projections 106 may be distributed in a non-uniform pattern on first side 114 of hydrophilic foam layer 104. In some embodiments, superabsorbent projections 106 may comprise one or more of nodules, dots, bumps, lumps, islands, and protuberances on first side 114 of hydrophilic foam layer 104. Superabsorbent projections 106 may be formed in a range of shapes such as squares, hexagons, hoops, stars, crosses, or a range of lines.

Second side 116 of hydrophilic foam layer 104 is shown to contact wound bed 118. In the embodiment shown in FIG. 4, hydrophilic foam layer 104 and drape layer 102 extend past the confines of and adhere to a top surface of the periwound 118. In other embodiments, hydrophilic foam layer 104 may lie entirely within the confines of the periwound 120.

Superabsorbent Projections

In some embodiments, wound dressing 100 includes a plurality of superabsorbent projections 106 extending from the first side 114 of hydrophilic foam layer 104. A top portion of superabsorbent projections 106 contacts second side 112 of drape layer 102. In some embodiments, superabsorbent projections 106 comprise a plurality of nodules, dots, bumps, lumps, islands, or protuberances.

In some embodiments, superabsorbent projections 106 may be formed from or otherwise include a superabsorbent polymer in the form of granules. The superabsorbent polymer may include Luquasorb 1160 or 1161, such as may be commercially available from BASF. The granules may be contained in a water soluble carrier polymer. One example of the water soluble carrier polymer is polyvinylpyrrolidone (PVP). The superabsorbent polymer of the superabsorbent projections 110 and the water soluble polymer may be formed into a slurry or a suspension using an organic solvent. The organic solvent may include propanone or propanol, and may aid in delivery of the superabsorbent projections 106 to the first side 114 of hydrophilic foam layer 104. In some embodiments, to increase the softness of the superabsorbent granules, a plasticizer may be added to the slurry. In one embodiment, the plasticizer may be water. In some embodiments, the slurry to form the superabsorbent projections 106 may have a formulation of 20 parts by mass of PVP, 10 parts by mass of a superabsorbent polymer, 1 part by mass of glycerol, and 100 parts by mass of propanone. In some embodiments, to plasticize the granules, 1 part to 2 parts by mass of water may be added to the slurry mixture. In other embodiments, a water soluble polymer superabsorbent precursor, such as acrylic acid or 2-acrylamido-2-methyl-propanesulfonic acid (AMPS), with suitable UV curing additives, may replace the superabsorbent polymer. Such a precursor may be a relatively low viscosity solution and can be printed onto hydrophilic foam layer 104 and exposed to UV light to form a soft gel, eliminating the need for a plasticizer. In some embodiments, the water soluble polymer superabsorbent precursor may be similar to that used for preparing hydrogel coatings.

The slurry mixture is applied to first side 114 of hydrophilic foam layer 104 to form superabsorbent projections 106. In some embodiments, the slurry may be applied to hydrophilic foam layer 104 through standard printing methods, such as silk screen printing, gravure printing, or by x-y plotter printing. Superabsorbent projections 104 may be in any non-contiguous shapes such as circles, squares, hexagons, hoops/halos, stars, crosses, a range of lines, or any combination of shapes. In some embodiments, superabsorbent projections 106 may have a diameter substantially within a range of between 4 mm to 6 mm, and in further embodiments the diameter may be 5 mm. Superabsorbent projections 106 may be printed such that they are substantially evenly distributed on first side 114. In other embodiments, superabsorbent projections 106 may be printed in an uneven (e.g. non-uniform, random, etc.) pattern on first side 114. In either embodiment, superabsorbent projections 106 are arranged in a non-contiguous manner (i.e. isolated, separated, spaced-apart, non-touching, etc.) so that a region remains between superabsorbent projections 106 to preserve flexibility of wound dressing 100. In some embodiments, superabsorbent projections 106 may include a flexible plasticized hydrophilic polymer matrix having a substantially continuous internal structure. In some embodiments, after the slurry mixture has dried in the pattern of superabsorbent projections 106, the superabsorbent projections 106 may be printed with an adhesive coated film to allow superabsorbent projections 106 to adhere to second side 112 of drape layer 102. In some embodiments, the adhesive applied to superabsorbent projections 106 is moisture vapor transmitting and/or patterned to allow passage of water vapor therethrough. The adhesive may include a continuous moisture vapor transmitting, pressure-sensitive adhesive layer of the type conventionally used for island-type wound dressings (e.g., a polyurethane or polyethylene-based pressure sensitive adhesive). One example of an adhesive which can be used is a pressure sensitive adhesive based on acrylate ester copolymers, polyvinyl ethyl ether and polyurethane, as described in Great Britain Patent Application No. 1280631A. The basis weight of the adhesive may be 20 to 250 g/m$^2$, and more preferably 50 to 150 g/m$^2$. In some embodiments, after the adhesive has been applied to superabsorbent projections 106, a surface head (i.e., an iron) is applied to drape layer 102 such that drape layer 102 bonds to the superabsorbent projections 106.

Superabsorbent projections 106 may be configured to swell upon absorption of fluid, such as wound fluid exudate. Superabsorbent projections 106 may be more hydrophilic than hydrophilic foam layer 104, such that superabsorbent projections 106 assist in wicking fluid from the second side 116 of the hydrophilic foam layer 104 towards the first side 114 and into the superabsorbent projections 106. Such high hydrophilicity of superabsorbent projections 110 establishes a hydrophilic gradient from the wound bed 118 to the atmosphere surrounding wound dressing 100. Each of the superabsorbent projections 106 may absorb and swell upon absorption of fluid, providing a visual indication of which portion of wound bed 118 has absorbed fluid. Superabsorbent projections 106 may swell and expand outwards, such that they approach the printed indicators 108 which surround a portion of superabsorbent projections 106. In some embodiments, superabsorbent projections 106 may be configured to swell and expand towards printed indicators 108 upon absorption of fluid such that printed indicators 108 provide a visual indication as to when superabsorbent projections 106 have reached a maximum absorption capacity. In some embodiments, upon absorption of fluid each of the superabsorbent projections 110 will remain isolated.

Printed Indicators

In some embodiments, wound dressing 100 includes a plurality of printed indicators 108 on the first side 110 of the hydrophilic foam layer 104. In the embodiment shown, printed indicators 108 are printed onto first side 114 of hydrophilic foam layer 104, such that they surround one or more of the superabsorbent projections 106. In the embodiment shown, printed indicators 108 surround the superabsorbent projections 106 in the central portion and corner portions of the wound dressing 100. In other embodiments, printed indicators 108 may surround any number and location of superabsorbent projections 106. Printed indicators 108 may be applied to hydrophilic foam layer 104 prior to assembly of the wound dressing 100. Printed indicators 108 may contact second side 112 of drape layer 102. In other embodiments, printed indicators 108 may be printed onto second side 112 of drape layer 102. Printed indicators 108 may contact first side 114 of hydrophilic foam layer 104. In still other embodiments, printed indicators 108 may be printed onto first side 110 of drape layer 102, such that they are exposed to the surrounding atmosphere.

Printed indicators 108 may be formed or otherwise include a dye. In some embodiments, a range of dyes may be used to form printed indicators 108 to achieve a biocompatible printed surface. In other embodiments, printed indicators 108 may be formed from a fluid-reactive dye, such that printed indicators 108 are not visible until wound dressing 108 begins to absorb wound fluid exudate. In still other embodiments, printed indicators 108 may be formed from a fluid-triggered wax, such that they are triggered when the surface printed indicators 108 are applied to, such as hydrophilic foam layer 104 or drape layer 102, has reached the maximum absorption capacity. In some embodiments, printed indicators 108 may be applied to hydrophilic foam layer 104 or drape layer 102 through standard printing methods, such as silk screen printing, gravure printing, or by x-y plotter printing.

Printed indicators 108 may be in any non-contiguous shapes such as circles, squares, hexagons, hoops/halos, stars, crosses, a range of lines, or any combination of shapes. In some embodiments, the shape of printed indicators 108 may match the shape of the superabsorbent projections 106 that they surround, such that if the superabsorbent projections 106 are circular, the surrounding printed indicators 108 are also circular. In some embodiments, printed indicators 108 may comprise a circular ring, and have a line width substantially within a range of between 8 mm and 10 mm. In some embodiments, the ratio of the diameter of the superabsorbent projections 106 to the diameter of the printed indicators 108 is substantially within a range of 1:1.6 to 1:2, and in further embodiments the ratio may be 1:1.8. The printed indicators 108 may have a diameter substantially within a range of between 8 mm and 10 mm, and in further embodiments the diameter may be 9 mm.

Method of Use and Test Results

Figure 5:
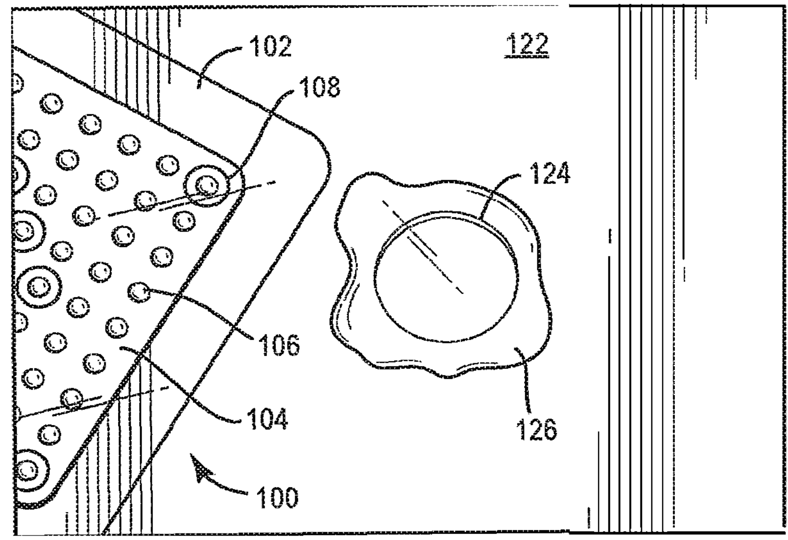
FIGS. 5-8 illustrate various stages of testing the absorption capacity of the wound dressing of FIGS. 1-2, according to an exemplary embodiment.

Referring now to FIGS. 5-8, a method of testing the performance of wound dressing 100 is shown, according to an exemplary embodiment. In FIG. 5, a fluid 126 is applied to a well 124 of a test surface 122 using a syringe. The well 124 is representative of a wound bed and the fluid 126 is representative of wound fluid exudate. In some embodiments, well 124 may be equivalent to wound bed 118. In other embodiments, other representative surfaces or methods may be used to test wound dressing 100. The fluid 126 is applied to well 124 such that the fluid 126 completely fills the well 124 and overflows onto the test surface 122 surrounding the well 124.

Figure 6:
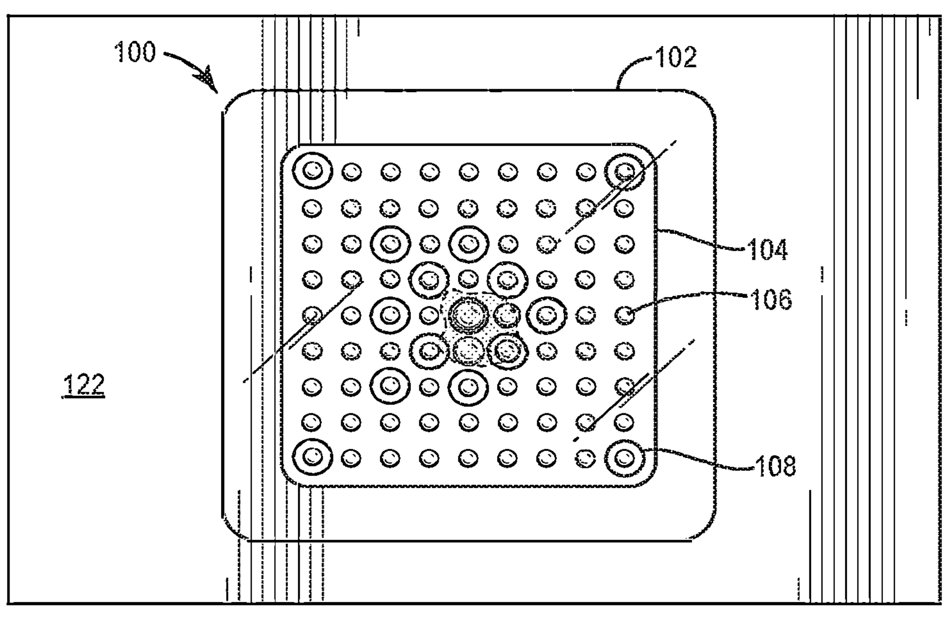

In the testing depicted in FIG. 6, 30 mL of fluid 126 has been applied to well 124. The wound dressing 100 has been placed over the test surface 122, such that a central portion of wound dressing 100 is aligned with the fluid 126 and the well 124. In the embodiment shown, wound dressing 100 comprises printed indicators 108 surrounding the superabsorbent projections 106 in a central zone and the four corner zones of wound dressing 100 to provide an indication of the level of absorption of wound dressing 100. The wound dressing 100 has been allowed to absorb fluid 126 for a period of approximately 1 hour. As shown in FIG. 6, wound dressing 100 has substantially fully absorbed the 30 mL fluid 126. Superabsorbent projections 106 have swollen and expanded outwards towards the printed indicators 108, but have not fully reached the printed indicators 108, thus indicating that the wound dressing 100 has not reached its maximum absorption capacity.

Figure 7:
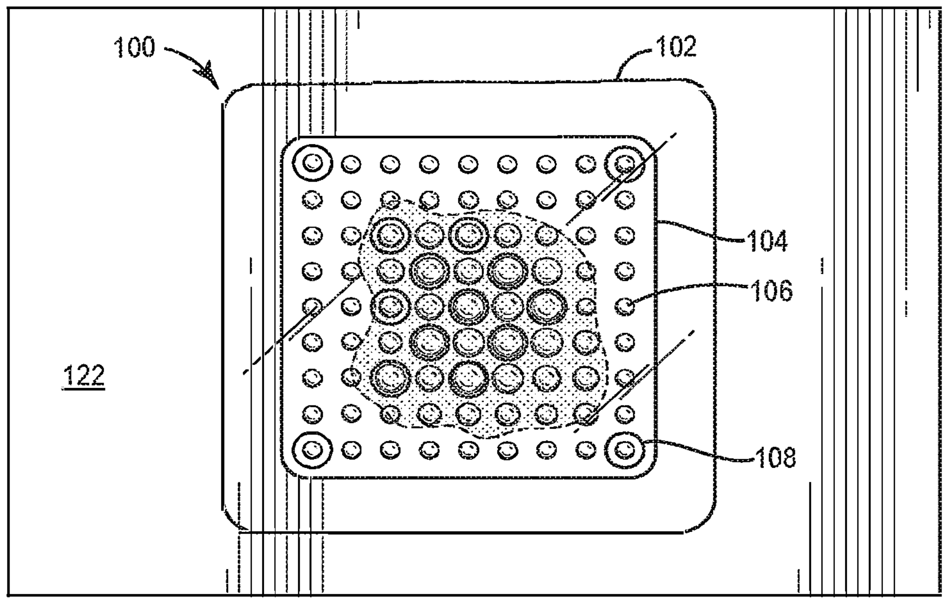

After wound dressing 100 has absorbed all 30 mL of fluid 126, wound dressing 200 was removed from the test surface 122. An additional 10 mL of fluid 126 was applied to well 124, and the wound dressing 100 has been placed back over the well 124, as seen in FIG. 7. Wound dressing 100 has been allowed to absorb the additional 10 mL of fluid 124 for a period of approximately 1 hour, such that the total fluid 126 absorbed by wound dressing 100 was 40 mL over a period of 2 hours. As seen in FIG. 7, all of the total 40 mL of fluid 126 has been fully absorbed by wound dressing 100. Superabsorbent projections 106 have swollen and expanded outwards towards the printed indicators 108, such that that the perimeter of superabsorbent projections 106 is substantially even with the perimeter of printed indicators 108, thus indicating that wound dressing 100 has reached its maximum absorption capacity upon the absorption of the total of 40 mL of fluid 126. In various other embodiments, wound dressing 100 may be configured to have an absorption capacity other than 40 mL, depending on the materials used to construct wound dressing 100, the size and spacing of superabsorbent projections 106, and a variety of other factors.

Figure 8:
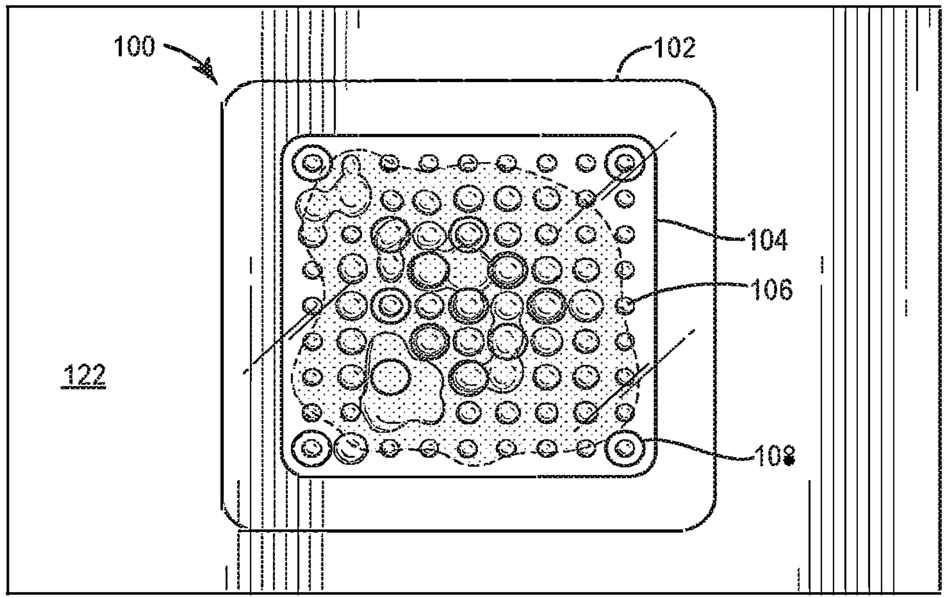

Referring now to FIG. 8, the wound dressing 100 was removed from test surface 122 and well 124 and was left to evaporate for a period of approximately 24 hours. As shown, the water content of the wound dressing 100 has significantly evaporated, as seen by the superabsorbent projections 106 shrinking or retracting away from printed indicators 108 such that the super absorbent projections have at least partially "dried out" and are now capable of re-absorbing fluid. At this time, it is believed that wound dressing 100 will have the same or similar properties or re-absorption capability after such evaporation has occurred.

According to an exemplary embodiment, wound dressing 100 has multiple advantages over previous wound dressings. Wound dressing 100 is both soft and flexible, and is capable of wicking fluid away from wound bed 136 and absorbing fluid over the plurality of non-contiguous superabsorbent projections 106. The printed indicators 108 surrounding the superabsorbent projections 106 provide a visual indication as to the dynamic change in hydration levels within the wound dressing 100. When superabsorbent projections 106 swell in response to the absorption of fluid by wound dressing 100, the printed indicators 108 provide a visual indication to a user as to if wound dressing 100 has reached maximum absorption capacity and needs to be changed or if wound dressing 100 still has absorption capability. Further, the printed indicators 108 may provide a visual indication as to when wound dressing 100 begins to lose fluid through evaporation, as the superabsorbent projections 106 begin to shrink back to their original size and move away from the printed indicators 108. The printed indicators 108 may also provide an indication of the level of hydration in the various regions or zones of wound dressing 100, which may provide a user with additional information about the wound itself. For example, certain regions of the dressing may show greater absorption than others, indicating locations in the wound bed where fluid is being produced, or may show that a periwound area remains dry. Additionally, the wound dressing 100 is relatively low-cost. The printed indicators 106 are a low-cost addition to provide a visual indication of hydration levels within wound dressing 100, and may further reduce overall cost by preventing a user from changing wound dressing 100 too frequently, such as when wound dressing 100 has not reached a maximum absorption capacity.

According to an exemplary embodiment, the superabsorbent polymer in the form of granules has a higher absorption capacity than traditionally used absorbent non-woven dressings and therefore can maintain the same absorption capacity as a traditional dressing with less material required. With less granules and material needed for the superabsorbent projections 106, the overall structure of wound dressing 100 is highly flexible and a thickness of wound dressing 100 may be reduced. Further, the concentration of superabsorbent polymer within the slurry may be increased to increase the absorption capacity of wound dressing 100 to have a high storage and fluid management capacity, or the print pattern and density of superabsorbent projections 110 may be changed to easily adapt the wound dressing 100 for a particular wound.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A method of making a wound dressing comprising:

providing a hydrophilic foam layer configured to engage a wound bed, and having a first side and a second side, the second side configured to face the wound bed;

preparing and applying a slurry comprising a superabsorbent material onto the first side of the hydrophilic foam layer in the form of a plurality of non-contiguous deposits;

printing one or more non-contiguous indicators onto the first side of the hydrophilic foam layer, such that the indicators surround one or more of the plurality of deposits; and placing a drape layer, having a first side and a second side, atop the hydrophilic foam layer.

2. The method of claim 1, wherein the deposits are configured to swell and expand towards the indicators upon absorption of fluid such that the indicators provide a visual indication as to when the deposits have reached a maximum absorption capacity.

3. The method of claim 1, further comprising printing the one or more indicators to surround the deposits in a central portion and one or more corner portions of the wound dressing.

4. The method of claim 1, wherein the indicators comprise a circular ring and have a line width substantially within a range of between 0.8 mm and 1.2 mm.

5. The method of claim 1, wherein the indicators have a diameter substantially within a range of between 8 mm and 10 mm.

6. The method of claim 1, wherein the deposits have a diameter substantially within a range of between 4 mm to 6 mm.

7. The method of claim 1, wherein a ratio of a diameter of the deposits to a diameter of the indicators is substantially within a range of 1:1.6 to 1:2.

8. The method of claim 1, further comprising printing the indicators onto the first side of the hydrophilic foam layer by screen printing, gravure printing, or by x-y plotter printing.

9. The method of claim 1, wherein the indicators comprise a fluid reactive dye.

10. The method of claim 1, further comprising laminating, via a fusible fiber, the drape layer to the hydrophilic foam layer.

11. The method of claim 1, wherein the deposits are operable to draw a wound exudate fluid through the hydrophilic foam layer.

12. The method of claim 1, wherein the hydrophilic foam layer comprises a fluid reactive dye configured to provide a visual indication of fluid absorption within the wound dressing.

13. The method of claim 12, wherein the fluid reactive dye comprises one of antherquinone, cothenile, and tartrazine.

14. A method of treating a wound, comprising:

providing a dressing configured to cover the wound, the dressing comprising a hydrophilic foam layer having a plurality of non-contiguous superabsorbent deposits and one or more non-contiguous printed indicators surrounding a corresponding one or more of the superabsorbent deposits;

observing, on the dressing, an amount of swelling of the superabsorbent deposits in response to the absorption of exudate from the wound; and replacing the dressing when edges of the swollen superabsorbent deposits approach the printed indicators within a predetermined range.

15. The method of claim 14, wherein the one or more printed indicators comprise a circular ring and have a line width substantially within a range of between 0.8 mm and 1.2 mm.

16. The method of claim 14, wherein the printed indicators have a diameter substantially within a range of between 8 mm and 10 mm.

17. The method of claim 14, wherein the superabsorbent deposits have a diameter substantially within a range of between 4 mm to 6 mm.

18. The method of claim 14, wherein a ratio of a diameter of the superabsorbent deposits to a diameter of the printed indicators is substantially within a range of 1:1.6 to 1:3 prior to the swelling of the superabsorbent deposits.

* * * * *